(12) United States Patent
Bonacum

(10) Patent No.: US 12,011,674 B2
(45) Date of Patent: Jun. 18, 2024

(54) WEARABLE FIDGET SPINNERS

(71) Applicant: Mindful Fidgets LLC, Standish, ME (US)

(72) Inventor: Kimberly Bonacum, Standish, ME (US)

(73) Assignee: Mindful Fidgets LLC, Standish, ME (US)

( * ) Notice: Subject to any disclaimer, the term of this patent is extended or adjusted under 35 U.S.C. 154(b) by 713 days.

(21) Appl. No.: 16/693,130

(22) Filed: Nov. 22, 2019

(65) Prior Publication Data

US 2020/0171399 A1 Jun. 4, 2020

Related U.S. Application Data

(60) Provisional application No. 62/775,260, filed on Dec. 4, 2018.

(51) Int. Cl.
*A63H 33/00* (2006.01)
*A61M 21/02* (2006.01)
*A61M 21/00* (2006.01)

(52) U.S. Cl.
CPC ............ *A63H 33/00* (2013.01); *A61M 21/02* (2013.01); *A61M 2021/0022* (2013.01); *A61M 2021/0044* (2013.01); *A61M 2205/59* (2013.01)

(58) Field of Classification Search
CPC .......... A61M 2021/0022; A61M 21/02; A61M 2205/59; A61M 2209/088; A61M 2210/083; H63H 33/00; H63H 1/00
See application file for complete search history.

(56) References Cited

U.S. PATENT DOCUMENTS

2008/0155788 A1* 7/2008 Wilcox .................. A43B 23/24
24/3.1
2018/0200638 A1 7/2018 Chin
2018/0352829 A1* 12/2018 Diamond ................. A44C 9/00

OTHER PUBLICATIONS

Wish; Fidget spinner wristband finger spinner bracelet hand toy for kids anxiety stress relief focus handspinner bangle toys; 4 pages; retrieved from the internet (https://www.wish.com/product/fidget-spinner-wristband-finger-spinner-bracelet-hand-toy-for-kids-anxiety-stress-relief-focus-handspinner-bangle-toys-gift-3-colors-5970d71aS57b185709dda3f447&hide_login_modal=true&share=web) on Mar. 3, 2021
Youtube; How to make a fidget spinner bracelet; (Screenshot); 2 pages retrieved from the internet (https://www.youtube.com/watch?v=k2q-z-mJG5Y) on Mar. 3, 2020.

* cited by examiner

*Primary Examiner* — Christine H Matthews
(74) *Attorney, Agent, or Firm* — Shay Glenn LLP

(57) ABSTRACT

Wearable devices that provide tactile, visual stimulation, and movement/manipulation for a user are described. The devices can include a spinner that rotates with respect to a base. The spinner can be spun by the user to produce visual stimulation that the user may find pleasing and soothing, and which may provide therapeutic effects. The spinner may also include tactile features, such as a series of protrusions and recesses, that the user can touch or rub to create a tactile sensation, which may also help the user to relieve and/or regulate stress. The spinner also allows the user to manipulate the spinner with fingers in small repetitive movements that may reduce restlessness. The devices may be sized and shaped such that the user may uninterruptedly perform everyday tasks and discretely wear and use the devices in certain social environments such as the classroom.

27 Claims, 18 Drawing Sheets

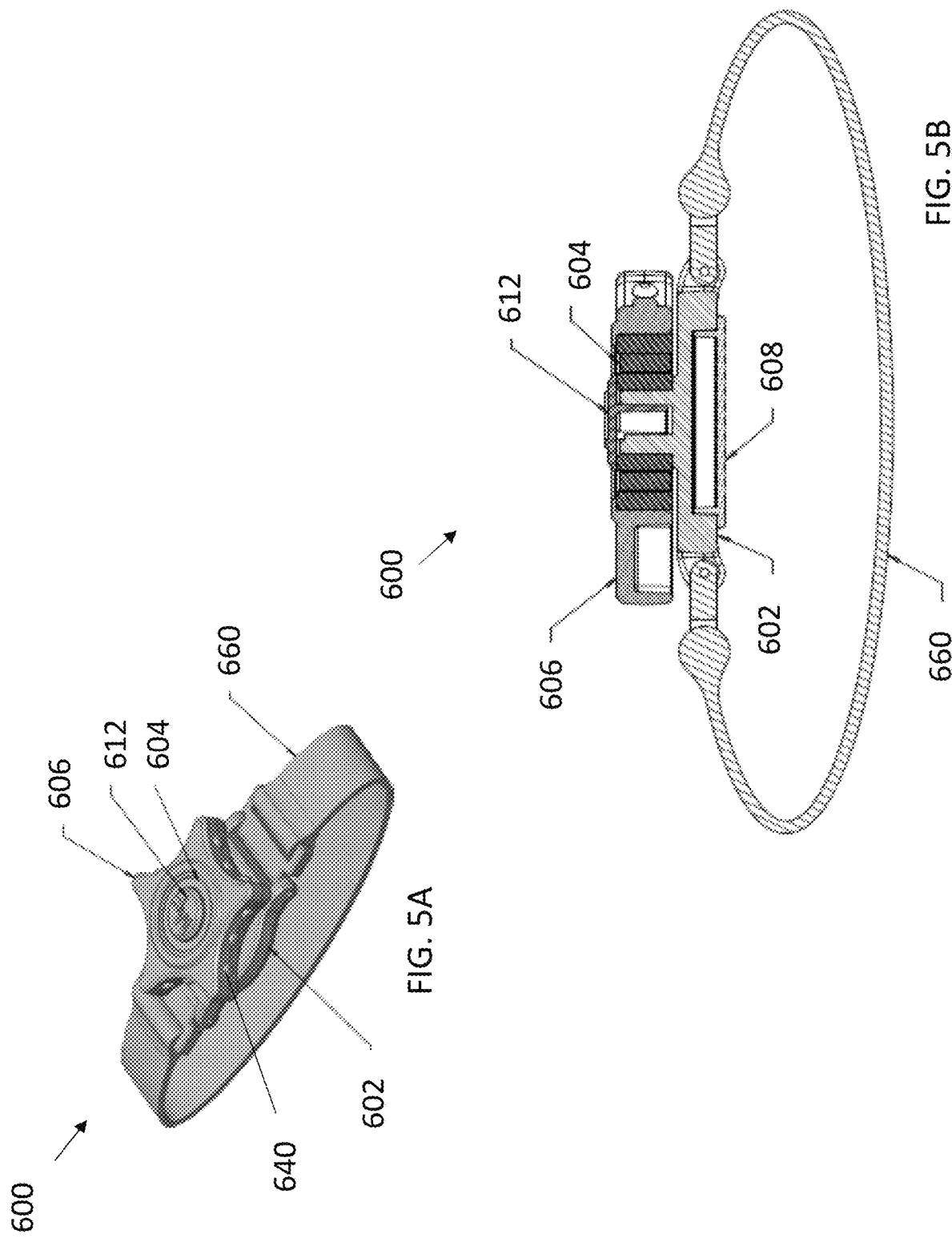

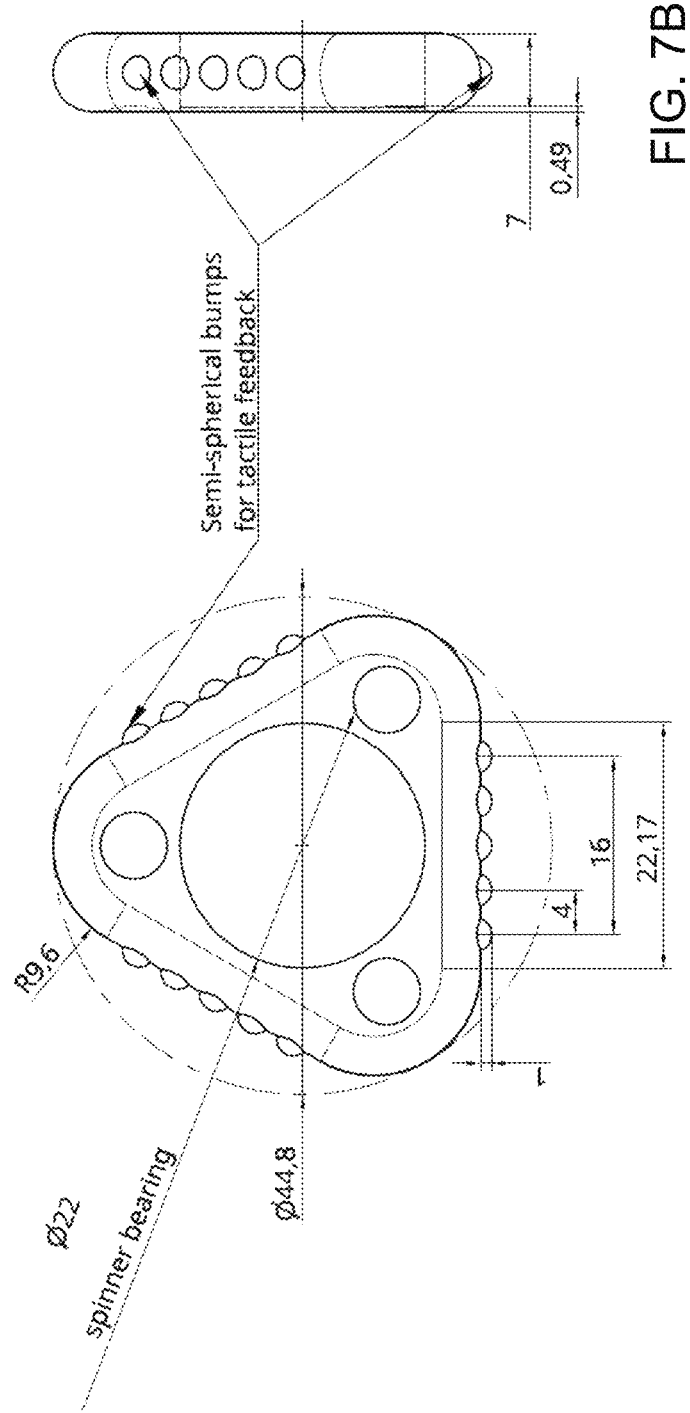

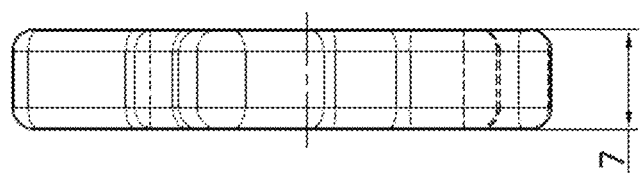
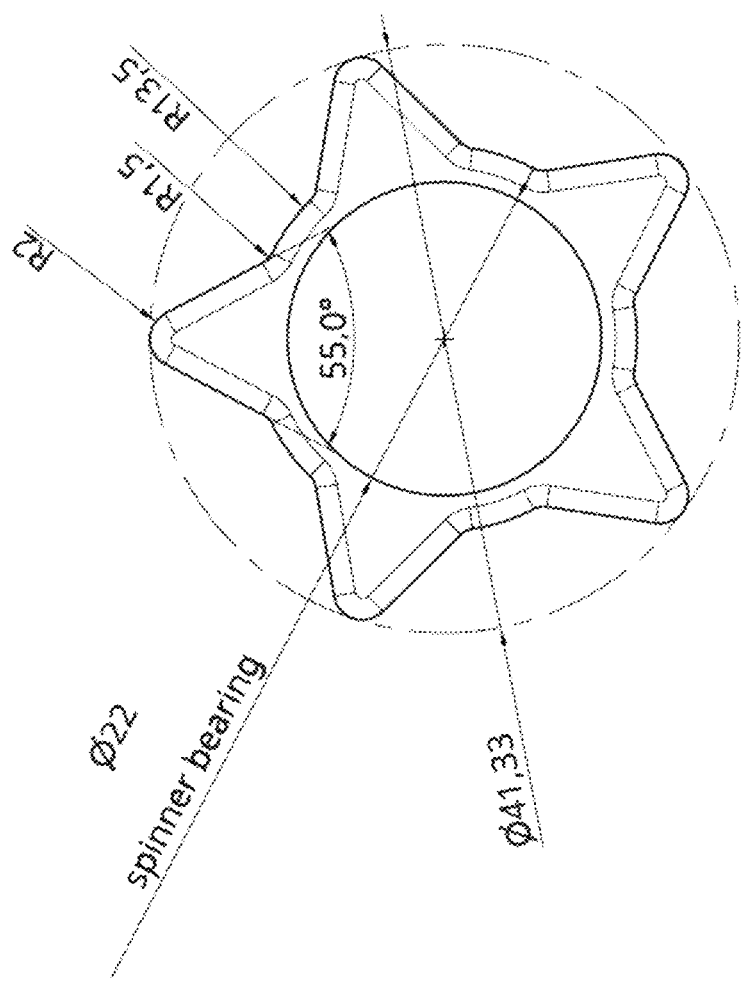
FIG. 9B
FIG. 9A

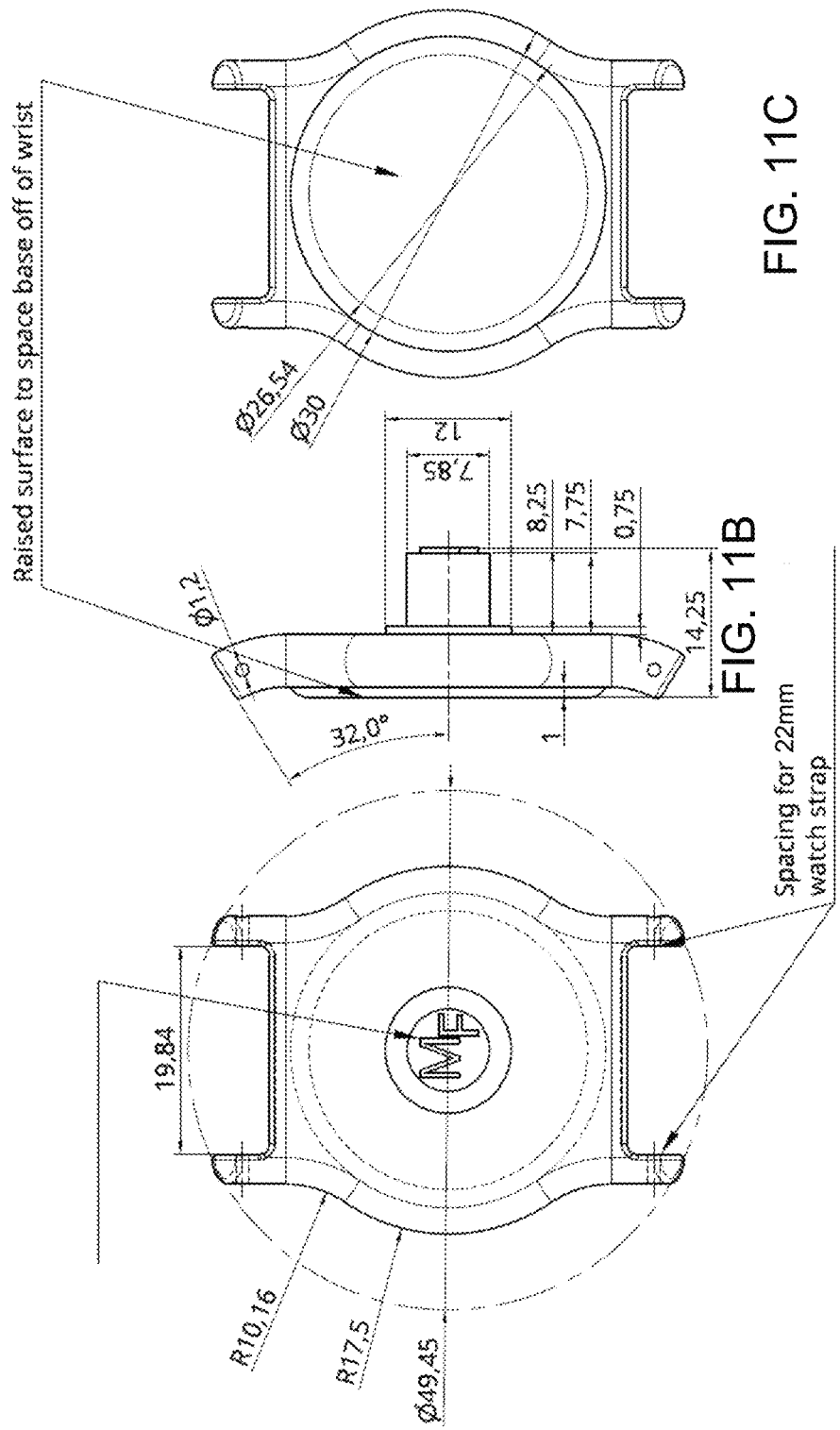

WEARABLE FIDGET SPINNERS

CROSS-REFERENCE TO RELATED APPLICATIONS

This application claims priority to U.S. Provisional Patent Application No. 62/775,260, filed on Dec. 4, 2018, titled "WEARABLE FIDGET SPINNERS," the entirety of which is incorporated by reference herein.

BACKGROUND

Many people find it helpful to hold and manipulate objects as way to relive stress and/or self-regulate. Stress balls, stretchable putty and other objects that a person can manipulate with their hands have recently gained popularity, not only as toys but also as stress-relieving therapeutic objects. Some theorize that these objects may help a person feel less anxious by re-directing nervous energy toward manipulating the object. Some students find these objects help them to attend better to lessons, focus better on assignments and keep calm during tests. Unfortunately, these stress-relieving objects are sometimes regarded as only toys, and they can be distracting for the user or for others around them. Some schools have even banned some of these objects from the classroom. This can be a disservice to students who find such objects beneficial while at school and in the classroom. What is needed, therefore, are stress-relieving objects that are less distracting and appropriate for a variety of settings, such as the classroom.

SUMMARY OF THE DISCLOSURE

Described herein are wearable devices and methods of their use. In particular, the wearable devices include features that allow users to manipulate the devices for therapeutic purposes/effect (e.g., to relieve stress and/or self-regulate). The wearable devices can include a spinner that a user can spin for therapeutic effect. In some cases, the devices allow a user to manipulate features of the devices in small repeated movements. The wearable devices may be sized and shaped such that the user may perform everyday tasks while wearing the devices. Aspects of the devices can make them appropriate for wearing in public and discretely in certain situations, such as classroom settings.

In general, in one embodiment, a wearable device includes a band, a base, and a spinner. The band is configured to be placed around a user's wrist. The base is attached to the band. The base includes a rotating mechanism configured to rotate about an axis and a first peripheral edge defining a base radius with respect to a center of the base. The spinner is coupled with the rotating mechanism and is axially aligned with the base so as to rotate with respect to the base. The spinner includes a second peripheral edge that projects radially with respect to the first peripheral edge. The second peripheral edge defines a second radius of the spinner with respect to the center of the base that is about 5 percent to about 40 percent larger than the base radius.

This and other embodiments can include one or more of the following features. The center of the base can align with the axis of rotation of the rotating mechanism. The first radius can be measured laterally across the base. The spinner can include an outer surface with at least one tactile feature. The at least one tactile feature can include a protrusion or a recess. The at least one tactile feature can be on the second peripheral edge. The at least one tactile feature can include at least one recess along the second peripheral edge of the spinner. A ratio of a depth of the at least one recess to a diameter of the spinner can range from about 0.5 to about 1. The tactile feature can include at least one recess along the second peripheral edge of the spinner that defines a minimum diameter of the spinner and at least one protrusion along the second peripheral edge of the spinner that defines a maximum diameter of the spinner, and a ratio between the maximum diameter to the minimum diameter can range from about 1.02 to about 1.06. The at least one tactile feature can be on a top surface of the spinner. The spinner can have a disc shape. The second peripheral edge of the spinner can form a flower, a star or a triangle shape. The rotating mechanism can include a bearing assembly.

In general, in one embodiment, a wearable device includes a band, a base, and a spinner. The band is configured to be placed around a user's wrist. The base is attached to the band. The base includes a rotating mechanism configured to rotate about an axis. The base includes a first peripheral edge defining a base radius with respect to a center of the base. The spinner is coupled with the rotating mechanism and axially aligned with the base so as to rotate with respect to the base. The spinner includes a second peripheral edge that projects radially with respect to the first peripheral edge. The spinner includes at least one tactile sensory feature thereon.

This and other embodiments can include one or more of the following features. The center of the base can align with the axis of rotation of the rotating mechanism. The spinner can include an outer surface with the at least one tactile sensory feature. The at least one tactile sensory feature can include a protrusion or a recess. The at least one tactile sensory feature can be on the second peripheral edge. The tactile sensory feature can include at least one recess along the second peripheral edge of the spinner. A ratio of a depth of the at least one recess to a diameter of the spinner can range from about 0.01 to about 0.03. The tactile sensory feature can include at least one recess along the second peripheral edge of the spinner that defines a minimum diameter of the spinner and at least one protrusion along the second peripheral edge of the spinner that defines a maximum diameter of the spinner. A ratio between the maximum diameter to the minimum diameter can range from about 1.02 to about 1.06. The at least one tactile sensory feature can be on a top surface of the spinner. The spinner can have a disc shape. The rotating mechanism can include a bearing assembly. The second peripheral edge of the spinner can form a flower, a star or a triangle shape.

In general, in one embodiment, a method of treating a disorder includes applying a band of a device to a wrist of a user, rotating a spinner about a base of the device to provide a therapeutic effect, and rubbing or moving a tactile feature on the spinner to provide additional therapeutic effect.

This and other embodiments can include one or more of the following features. The user can suffer from attention deficit hyperactivity disorder (ADHD), anxiety, depression, specific learning disability (SLD), Alzheimer's, autism, or akathisia. The therapeutic effect can be relief of stress, reducing excess energy, or reducing symptoms of the disorder. The tactile feature can be a bump on a peripheral edge of the spinner. The base can include a first peripheral edge defining a base radius with respect to a center of the base, and the spinner can include a second peripheral edge that projects radially with respect to the first peripheral edge. The second peripheral edge can define a second radius of the spinner with respect to the center of the base that is about 5 percent to about 40 percent larger than the base radius.

BRIEF DESCRIPTION OF THE DRAWINGS

Novel features of the devices and methods are set forth with particularity in the claims that follow. A better understanding of the features and advantages thereof will be obtained by reference to the following detailed description that sets forth illustrative embodiments, in which the principles of the described embodiments are utilized, and the accompanying figures.

FIG. 5A shows an isometric view of another exemplary wearable device; FIG. 5B shows a cross-sectional view of the wearable device of FIG. 5A.

FIG. 6A is a front, top, left perspective view of the wearable fidget device; FIG. 6B is a rear plan view of the wearable fidget device of FIG. 6A.

FIG. 6C is a front plan view of the wearable fidget device of FIG. 6A. FIG. 6D is a left plan view of the wearable fidget device of FIG. 6A. FIG. 6E is a right plan view of the wearable fidget device of FIG. 6A. FIG. 6F is a top plan view of the device of FIG. 6A. FIG. 6G is a bottom plan view of the device of FIG. 6A. In some embodiments, the broken lines represent a portion of the structure that forms no part of a design claim.

FIGS. 7A-7B show exemplary dimensions for a triangle-shaped spinner.

FIGS. 9A-9B show exemplary dimensions for a star-shaped spinner.

FIGS. 11A-11C show exemplary dimensions for various features of an exemplary base.

DETAILED DESCRIPTION

Figure 1B:
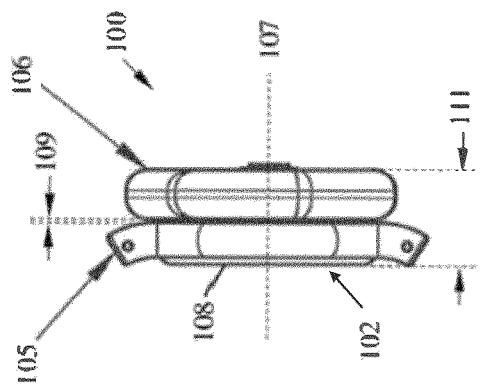
FIG. 1B shows a side view of the wearable device of FIG. 1A.
Figure 1D:
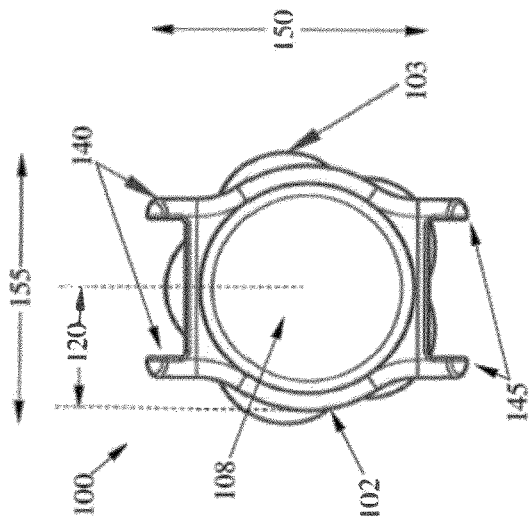
FIG. 1D shows a back view of the wearable device of FIGS. 1A-1C and 1E.
Figure 1A:
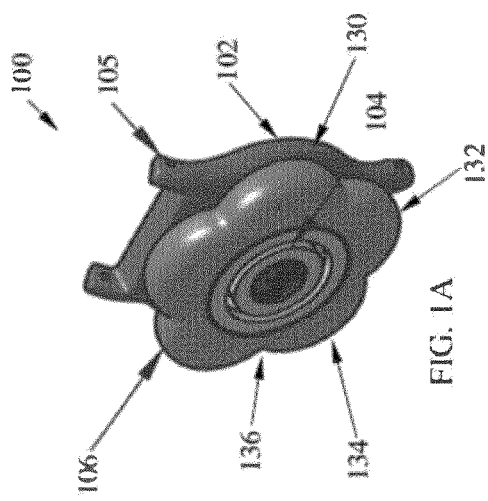
FIG. 1A shows an isometric view of an exemplary wearable device.
Figure 1C:
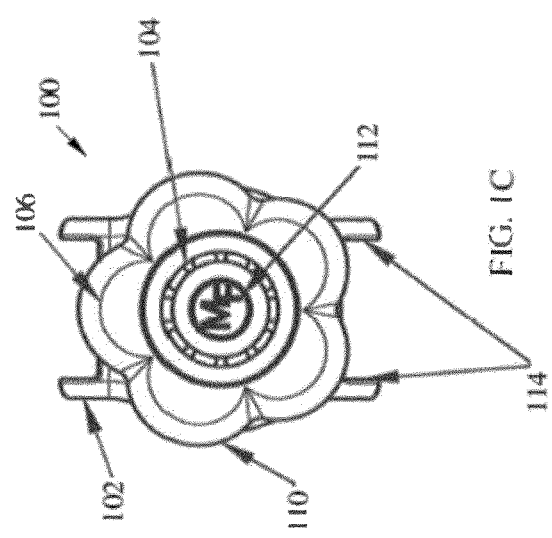
FIGS. 1C and 1E show front views of the wearable device of FIGS. 1A and 1B.
Figure 1E:
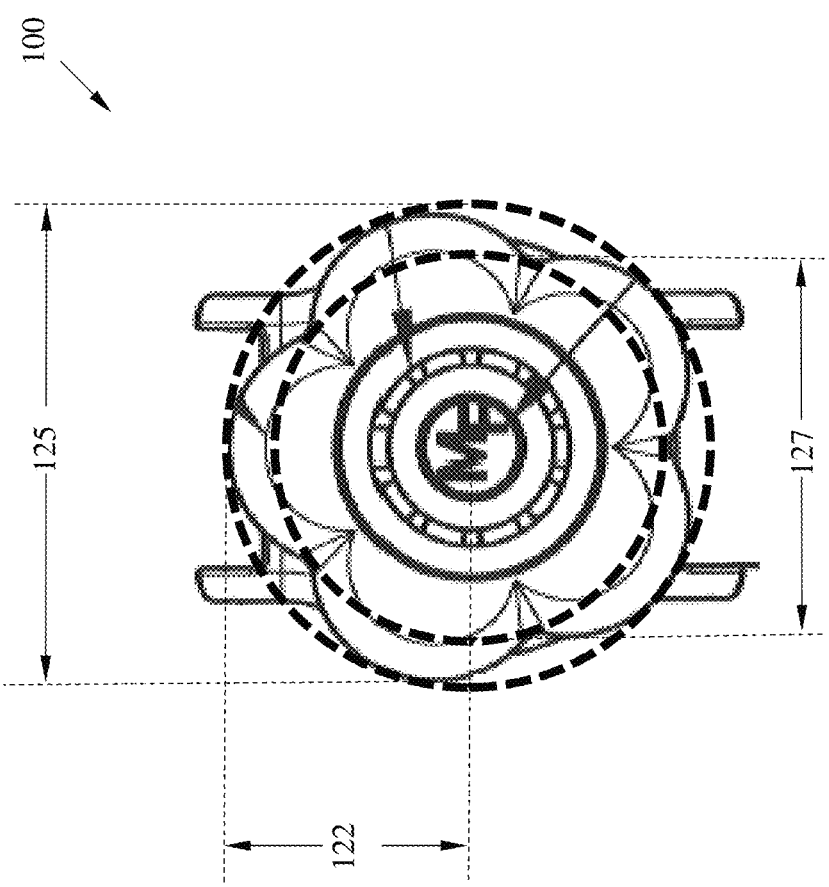
Figure 2A:
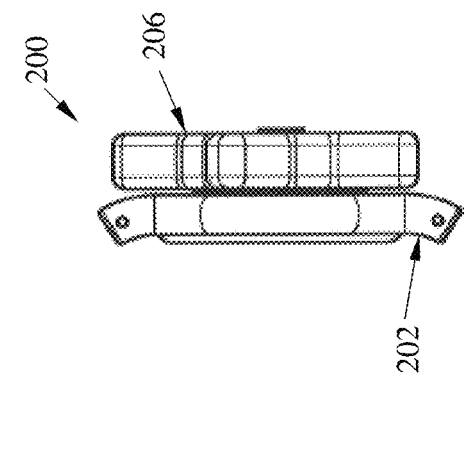
FIG. 2A shows an isometric view of another exemplary wearable device.
Figure 2B:
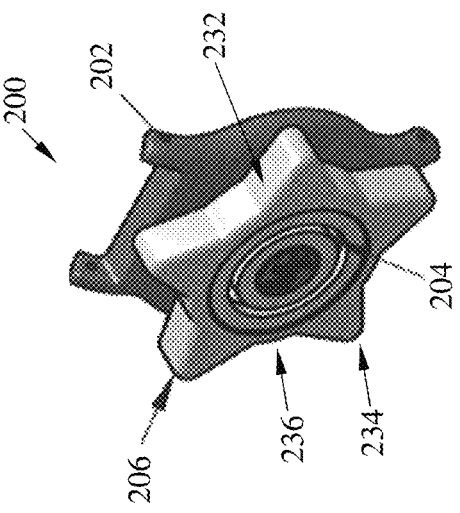
FIG. 2B shows a side view of the wearable device of FIG. 2A.
Figure 2C:
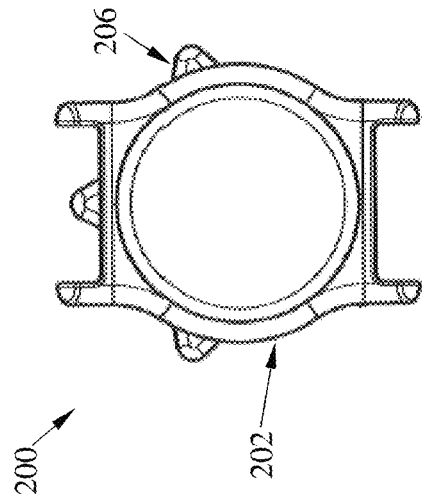
FIG. 2C shows a front view of the wearable device of FIGS. 2A and 2B.
Figure 2D:
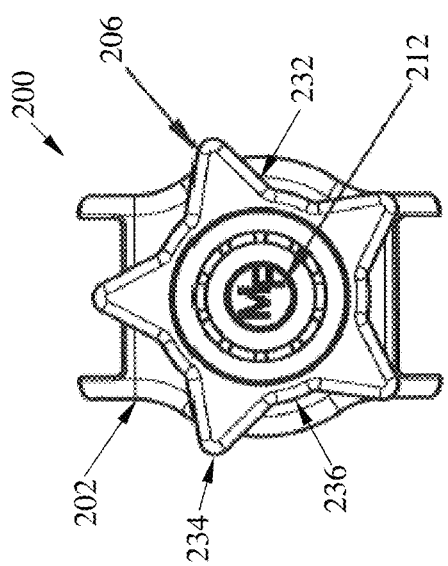
FIG. 2D shows a back view of the wearable device of FIGS. 2A-2C.
Figure 3B:
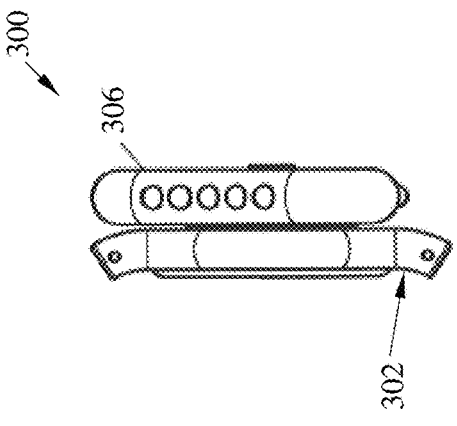
FIG. 3B shows a side view of the wearable device of FIG. 3A.
Figure 3D:
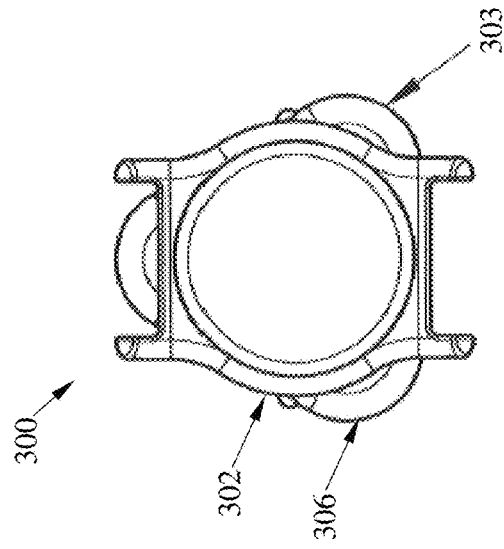
FIG. 3D shows a back view of the wearable device of FIGS. 3A-3C.
Figure 3A:
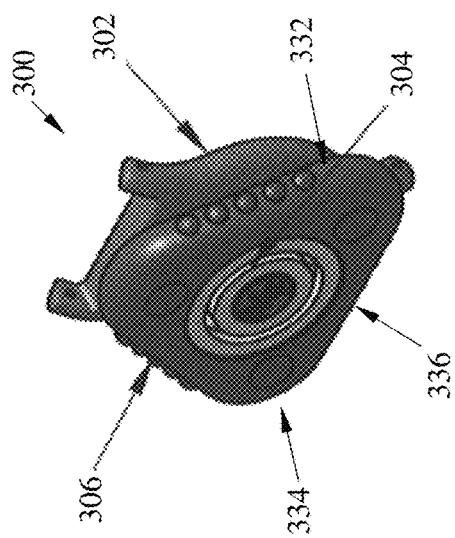
FIG. 3A shows an isometric view of a further exemplary wearable device.
Figure 3C:
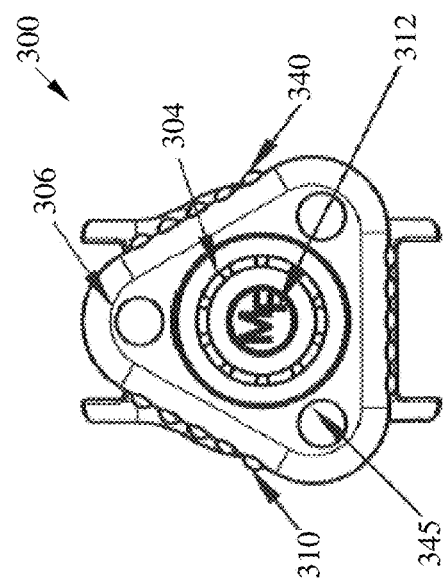
FIG. 3C shows a front view of the wearable device of FIGS. 3A and 3B.

Described herein are devices that may be used as tools for therapeutic purposes (e.g., to relieve stress and/or support self-regulation, such as addressing excess energy). The devices may include a spinnable member (also referred to as a spinner) that is configured to rotate under a user's control for movement and visual sensory input. In some cases, the devices include one or more tactile features that a user can touch and/or rub for tactile sensory input. Thus, the user can choose to spin the spinner, such as with his or her fingers (movement manipulation), regard it spinning (visual sensory input), touch/or rub the tactile features, or engage all three. In some embodiments, the devices can have a small profile such that the device may be worn on a user's body and/or on or under a user's clothing (e.g., on the user's wrist under clothing).

FIGS. 1A-1E show an exemplary wearable device 100 in accordance with some embodiments. The device 100 can include a base 102, a rotating mechanism 104, and a spinner 106. The rotating mechanism 104 can be coupled to the base 102 such that the rotating mechanism 104 can rotate with respect to the base 102. In some embodiments, the rotating mechanism 104 corresponds to or includes a bearing assembly. The rotating mechanism 104 can rotate with respect to an axis 107, which may or may be substantially aligned with a center of the base 102 and/or the spinner 106. The spinner 106 can be coupled with the rotating mechanism 104 and axially aligned with the base 102 such that the spinner 106 can rotate with respect to the base 102. The spinner 106 (e.g., a bottom surface thereof) may be offset from the base 102 (e.g., a top surface thereof) by a gap 109, which can allow the spinner 106 to rotate freely with respect to the base 102. In some cases, the spinner 106 and base 102 are axially aligned such that the gap 109 has a substantially uniform height. In some cases, a back side of the base 102 includes a standoff 108 that is positioned between a main portion of the base 102 and a person's wrist. The standoff 108 may allow the device 100 to rest slightly elevated from the wearer's wrist so that the spinner 106 can spin freely, for example without bumping the wrist. In some cases, the device 100 includes a cap 112 that covers the underlying rotating mechanism 104, and which may prevent debris from entering the rotating mechanism 104. The cap 112 may be a separate piece or may be a part of (e.g., integrally formed with) the spinner 106, and may include indicia such as a logo. In some embodiments, the device 100 does not include the cap 112 such that a portion of the rotating mechanism 104 is exposed. The wearable devices described herein can include any number of rotating mechanisms (e.g., bearing assemblies). In some cases, it is beneficial for the device to include a single rotating mechanisms (e.g., as opposed to three) to make the device smaller and lighter and better suited for being worn.

The base 102 can be configured to couple with a wristband (or other wearable element). The base 102 can include one or more attachment features 105 configured to couple the base 102 to the wristband. For example, the attachment features 105 can correspond to prongs or lugs that may engage with or otherwise couple to corresponding portions of a wristband. In some cases, the attachment features include holes, for example, for accepting fasteners (e.g., pins or screws). The attachment features 105 may be situated on opposing sides of the base 102 in a longitudinal direction 150 such that a first portion of the wristband can be coupled to a first set 140 of attachment features 105 and a second portion of the wristband can be coupled to a second set 145 of attachment features 105. The attachment features 105 of each set 140, 145 may be spaced apart by a predetermined distance 114 (e.g., about 20 millimeters), such as for a standard sized wristband (e.g., 20 millimeters). In some embodiments, the attachment features 105 may be configured to engage with the wristband via a quick release mechanism. This can allow the base 102 to be easily coupled with different wristbands, e.g., having different colors, textures, widths, lengths, etc. In some embodiments, the base 102 can be configured to couple with a bracelet, such as a silicon bracelet.

One of the advantages of the device 100 being wearable is that the user can access to and use the device 100 (e.g., therapeutically) throughout the day. For example, the user can spin the spinner 106 when feeling anxious during a certain activity, such as during a classroom lesson or a test. The user can then choose to stop spinning of the spinner 106 to perform a different activity, such as writing or typing, or when it is inappropriate to manipulate the device 100. Since the device 100 is worn on the user, it is immediately accessible to the user as needed. In this way, the device 100 provides control for the user to choose when to manipulate the device 100 for therapeutic effect.

The device 100 can have features that minimize distraction for the wearer of the device 100. For example, device 100 can be small to allow the wearer to engage in their daily tasks without the device 100 getting in the way (e.g., as a larger one may). A small device 100 may allow the wearer to wear the device 100 in activities such as writing, typing, getting dressed and physical activity (e.g., sports, physical education class) in an unobstructed manner and without the need to remove the device 100. A small device can also allow the device to be worn under a jacket or a long sleeve shirt with little interference. Thus, a smaller device 100 may allow the device 100 to be immediately available since the user may wear the device 100 throughout the day. Further, a small device 100 may allow the user to wear and use the device 100 more discretely than a larger device. The device 100 may have a low profile, i.e., having a small thickness 111. In some embodiments, the device 100 has a thickness of at most about 21 millimeters. In some cases, the base 102 and/or the spinner 106 are disc-shaped with substantially flat opposing sides (e.g., top and bottom sides). In some embodiments, the base 102 has a thickness of at most about 14 millimeters. In some embodiments, the spinner 106 has a thickness of at most about 7 millimeters. The diameter 125 of the device 100 may also be small to minimize the amount that the edges of the device 100 protrudes from the wearer's wrist. This can reduce the chances of the spinner 106 from hitting, for example, the back of the hand adjacent the wrist. The diameter 125 of the device 100 may vary depending on the wearer. For example, the diameter of the device 100 may be smaller for children users compared to adult users. In some cases, a maximum diameter of the device 100 corresponds to a maximum diameter of the spinner 106. In some embodiments, the diameter 125 of the spinner 106 ranges from about 39 millimeters to about 44 millimeters. In some embodiments, the diameter 120 of the base 102 ranges from about 35 millimeters to about 50 millimeters.

In some cases, the spinner 106 may have a prescribed size in relation to that of the base 102. For example, it may be beneficial for a radius 125 of the spinner 106 to be small enough in relation to a radius 120 of the base 102 to reduce the chances of the spinner 106 contacting a person's wrist, hand or other object, thereby allowing the spinner 106 to rotate freely. On the other hand, it may be beneficial for the radius 122 of the spinner 106 to be large enough in relation to a radius 120 of the base 102 for a user to easily access a peripheral edge 132 of the spinner 106 in order to touch and/or spin the spinner 106. In some cases, at least a portion of the radius 122 of the spinner 106 is larger than the radius 120 of the base 102. That is, the peripheral edge 130 of the base 102 can define a first radius 120, and the peripheral edge 132 of the spinner 106 can define a second radius 122 that is larger than the first radius 120. In some embodiments, the radius 125 of the spinner 106 may be from about 5 percent (%) to about 40% larger, from about 5% to about 30% larger, from about 5% to about 25% larger, from about 10% to about 40% larger, from about 10% to about 30% larger, or from about 10% to about 25% larger than the radius 120 of the base 102. The radius 120 of the base 102 may be measured along a lateral direction 155 (e.g., as opposed to a longitudinal direction 150). The radius 122 of the spinner 106 may correspond to a maximum radius of the spinner 106.

In some embodiments, the wearable devices described herein include one or more tactile sensory features for therapeutic effect, which can be used in addition to or as an alternative to the spinning aspects of the spinner. A tactile feature can correspond to a surface feature that the user can feel with one or more fingers. The tactile feature may be large enough for the user to detect with their finger, and small enough for a user's finger to rub across in small repeated motions (e.g., for stress reduction and/or self-regulation). The tactile feature may correspond to, for example, a protrusion, recess, or a combination of protrusions and recesses on an outer surface of the base and/or the spinner. The tactile feature may correspond to a series (e.g., pattern) of protrusions and recesses.

Returning to FIGS. 1A-1E, the peripheral edge 132 of the spinner 106 includes lobes 134 that can act as tactile features. The lobes 134 can correspond to a series of protrusions separated by recesses 136. The lobes 134 may be arranged symmetrically around the periphery of the spinner 106 to give the spinner 106 a flower-like shape. Edges along the outer surface of the spinner 106 can be rounded or curved (e.g., in an axial direction and/or a radial direction) to provide a smooth continuous contact surface. The lobes 134 can be smooth and curved separated by recesses 136 that provide breaks between the curved lobes 134. In some cases, a user can rub a recess 136 region between the lobes 134 in small repeated motions to provide a soothing for therapeutic effect.

In some cases, the depth of the recesses along the peripheral edge of the spinner can play a factor in how the tactile features provide stimulation. For example, the depth of the valleys 136 between lobes 134 may be large enough such that the user may feel the surface variation along peripheral edge 132, but small enough such that the diameter 125 of the spinner 106 is in accordance with a small device 100. In some embodiments, the depth of the recesses along the peripheral edge of the spinner ranges from about 0.5 millimeters to about 1 millimeter. Further, the relative size of the tactile features with respect to the rest of the device may contribute to the tactile aspects of the device. In some embodiments, the ratio of depth of the recesses along the peripheral edge of the spinner with respect to the diameter of the spinner ranges from about 0.01 to about 0.03. The maximum diameter of the spinner (e.g., 125) the with respect to a minimum diameter (e.g., 127) may also contribute to the tactile aspects of the device by allowing the tactile features along the peripheral edge of the spinner to be accessible. In some embodiments, the ratio between the maximum diameter of the spinner (e.g., 125) to the minimum diameter (e.g., 127) ranges from about 1.02 to about 1.06.

The tactile surface of the spinner 106 can be used alone or in combination with the spinning motion of the spinner 106 to relieve and regulate stress. In one example, the user may initiate spinning of the spinner 106 with one or more fingers to allow the spinner 106 to rotate freely for a period to provide therapeutic effect. In another example, the user may hold spinner 106 relatively steady with a hand while rubbing one or more of the tactile features (e.g., lobes 134) using one or more fingers. In further example, the user may rub one or more of the tactile features (e.g., lobes 134) using one or more fingers while partially rotating the spinner 106 in repeated small movements, such as rocking back and forth movements. In yet another example, the user may rub a tactile feature (e.g., lobes 134) for a period, spin the spinner 106 to allow the spinner 106 to freely spin for another period, and then stop the spinner 106 to rub the tactile feature (e.g., lobes 134) again. The user can choose any of a number of combination of rubbing, rocking and spinning sequences as desired. In this way, the user can experience varied tactile stimulation (e.g., rubbing, rocking and/or spinning) based on their preference and under their control.

The various parts of the device 100 (e.g., spinner 106, rotating mechanism 104 and base 102) can be made of material that is durable enough to withstand wear when exposed to everyday activities. In some embodiments, the rotating mechanism 104 is made of metal (e.g., steel), ceramic, or a combination thereof. In some embodiments, the base 102 and spinner 106 are made of a molded material, such as plastic, and/or a metal (e.g., aluminum or steel). In some cases, the base 102 and spinner 106 are made of the same material. The material may be any color or combination of colors. In some embodiments, the outer surface of the spinner (or portions thereof, such as the peripheral edge 132) has a smooth hard surface (e.g., made of a hard plastic), which may be tacitly pleasing. In some embodiments, the outer surface of the spinner (or portions thereof, such as the peripheral edge 132) is made of a flexible and resilient material that may have some give when pressed (e.g., silicone, rubber and/or flexible plastic). In some embodiments, the outer surface of the spinner (or portions thereof, such as the peripheral edge 132) is made of a combination of hard and flexible materials.

FIGS. 2A-2D show another exemplary device 200 similar to device 100. The device 200 includes a base 202, rotatable mechanism 204 and cap 212, similar to those of device 100 except that device 200 has a star-shaped spinner 306. The peripheral edge 232 can include a series of points 234 separated by valleys 236, which may be arranged symmetrically around the periphery of the spinner 206. The tops of the points 234 and the bottoms of the valleys 236 may be chamfered and/or curved to provide a smooth and continuous contact surface along the peripheral edge 232. In some cases, a user can rub the valley 236 region between the points 234 in small repeated motions to provide a soothing sensory input.

FIGS. 3A-3D show an exemplary device 300, which includes a base 302, rotatable mechanism 304 and cap 312, similar to devices 100 and 200 except that device 300 has a triangular shaped spinner 306. The peripheral edge 332 can include points 334 and sides 336, which may be arranged symmetrically around the periphery of the spinner 306. The tops of the points 334 may be chamfered and/or curved to provide a smooth and continuous contact surface. In some cases, the peripheral edge 332 includes bumps 340 (e.g., along sides 336), which can enhance a tactile experience. In some embodiments, a top surface of the spinner 306 includes concave dips 345, which can enhance a tactile experience. In some cases, a user can rub the bumps 340 and/or dips 345 in small repeated motions to provide a soothing therapeutic effect. As indicated by the bumps 340 and dips 345 of spinner 306, various surface of the wearable devices can include any of a number of combination of protrusions (e.g., bumps, bulges, knobs, etc.) and/or recesses (e.g., dips, dents, holes, cavities, etc.) as tactile features. In some embodiments, the protrusions (e.g., 340) and/or recesses (e.g., 345) protrude or recess with respect to the surrounding surface by about 0.75 millimeters to about 1.5 millimeters.

Figure 4B:
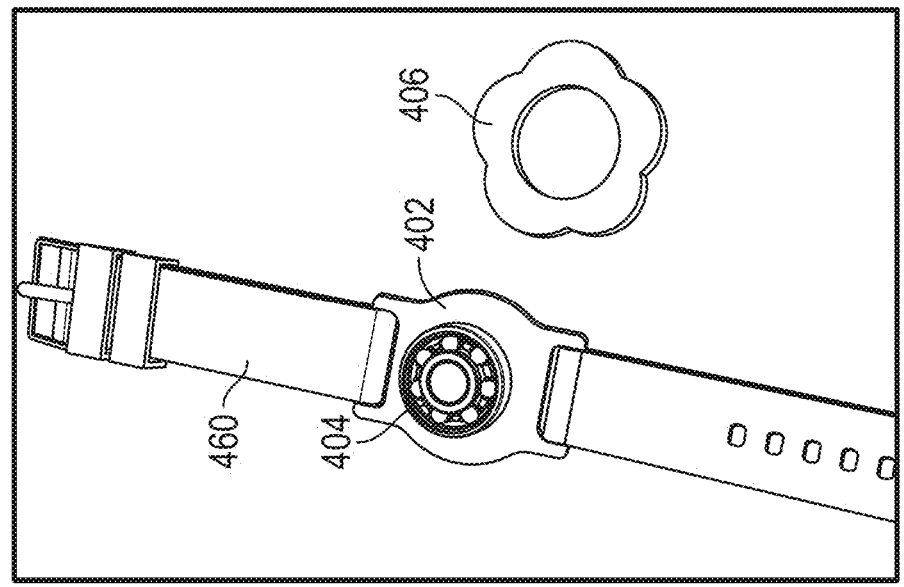
FIG. 4B shows the wearable device of FIG. 4A with a spinner.
Figure 4A:
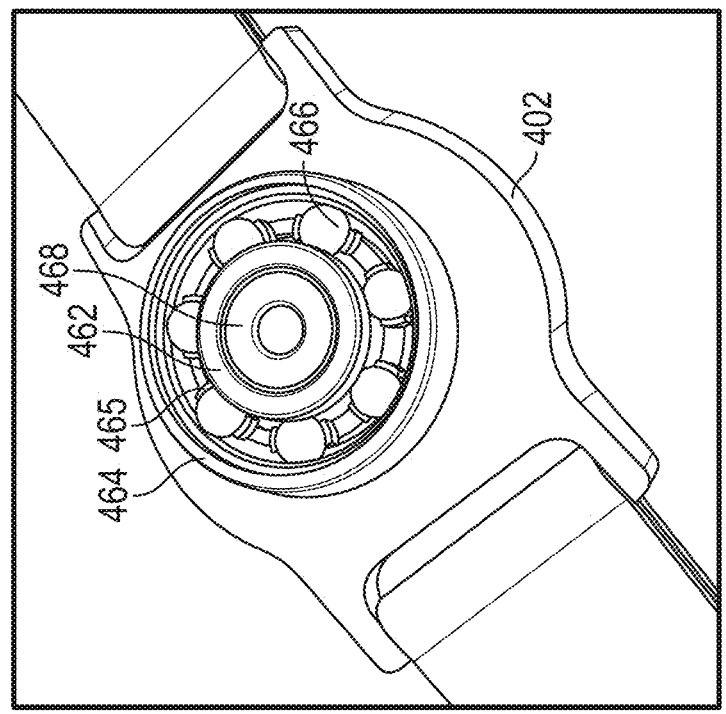
FIG. 4A shows a bearing assembly and base of a wearable device.
Figure 4C:
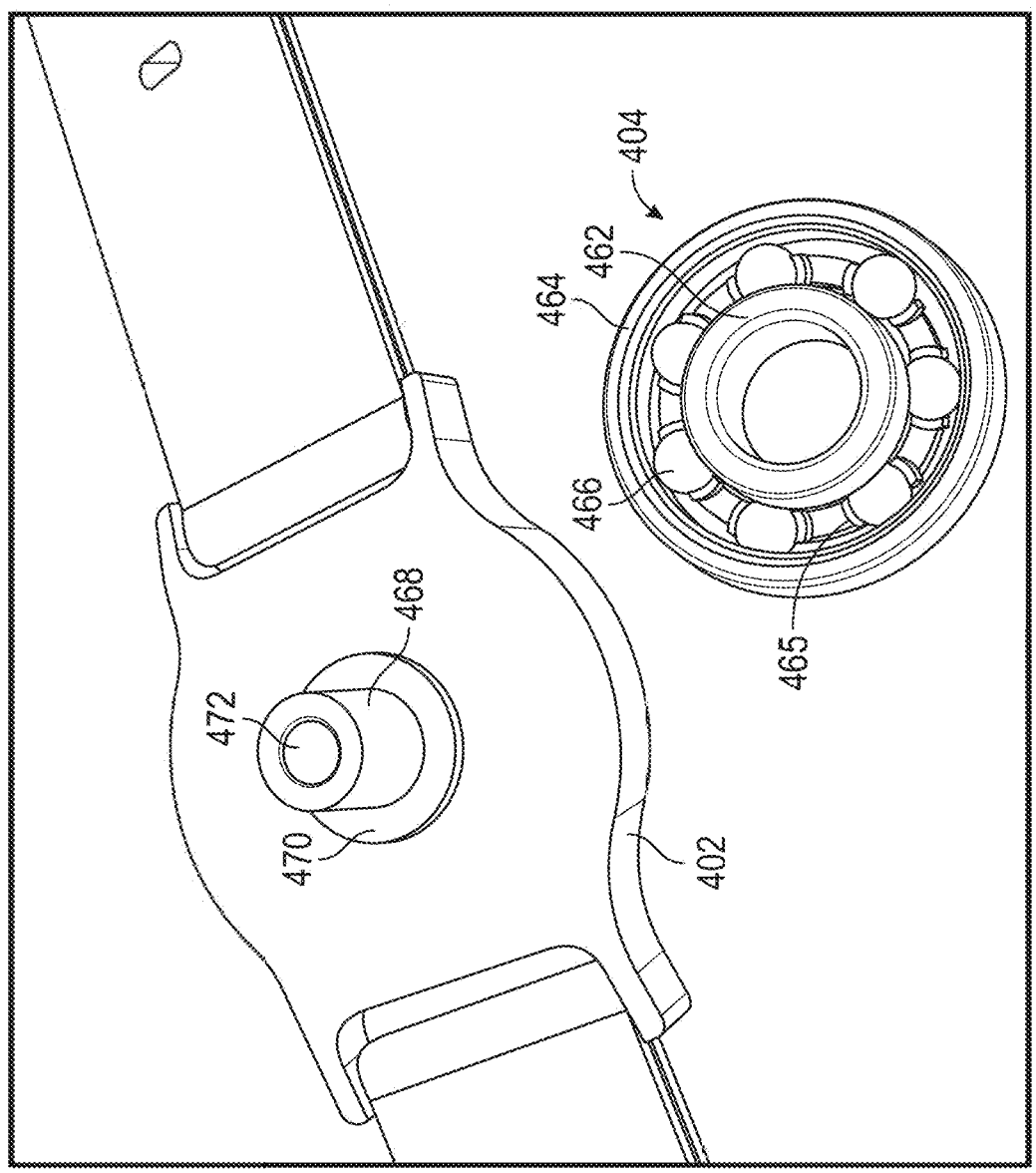
FIG. 4C shows the wearable device of FIGS. 4A and 4B with the bearing assembly disassembled from the base.

FIGS. 4A-4C show a disassembled exemplary wearable device 400, which includes a spinner 406, a base 402, a rotating mechanism 404 and a band 460. In device 400, the rotating mechanism 404 includes a bearing assembly having an inner ring 462, an outer ring 464, balls 466 and a ball retainer 465 (e.g., for maintaining spacing between the balls 466). In some embodiments, the outer ring 464 may be configured to rotate with respect to the base 402 and be coupled with the spinner 406. The size and configuration of the bearing assembly can vary. The bearing assembly may be lightweight so that it can be easily worn on the body or clothing. In some cases, the balls 466 are "608" type bearing balls. The balls 466 may be made of materials such as metal (e.g., steel) and/or ceramic. The inner ring 462 can be coupled with a post 468 that protrudes from the top surface of the base 402. The post 468 may be part of or coupled to the base 402. In some embodiments, the post 468 has a cylindrical shape (e.g., having parallel side walls) to engage with corresponding parallel side walls of the inner ring 462. This cylindrical shape may allow post 468 to fit more snuggly to corresponding parallel side walls of the inner ring 462 compared to, for example, a conical shaped post. The post 468 may have a substantially flat top surface aligned with a substantially flat top surface of the rotating mechanism 404 (see, e.g., FIG. 4A). A post 468 having a flat top may be safer than, for example, a post having pointy top, which may be hazardous near eyes. A flat top surface can also be in accordance with device 400 having a low profile. The post 468 may include a central opening 472 that is configured to accept a corresponding engagement member of a cap or a portion of the spinner. The post 468 may include a lip 470 that surrounds a lower portion of the post 468 at the base 402, which may act as a standoff to maintain a space between the rotatable outer ring 464 and the top surface of the base 402.

The various pieces of device 400 (e.g., the spinner 406, the base 402, the rotating mechanism 404 and the cap) may be coupled together using frictional fitting and/or adhesive. In some cases, it is beneficial for at least some of the pieces to be fixedly coupled together (e.g., with an adhesive). For example, an adhesive may be used to couple the spinner 406 to the rotating mechanism 404, and to couple the rotating mechanism 404 to the base 402. Fixedly coupling these components may assure that the rotating mechanism 404 and/or the spinner 406 does/do not separate during operation of the device 400 (e.g., spinning), which may reduce the chances of these components becoming choking hazards (e.g., for children). Further, a fixed base 402, rotating mechanism 404 and spinner 406 assembly can prevent the user from disassembling and playing with these components in distracting ways (e.g., throwing the spinner 406 across room). Any suitable type of adhesive can be used, including adhesives configured to adhere different types of material (e.g., metal and plastic).

Figure 5C:
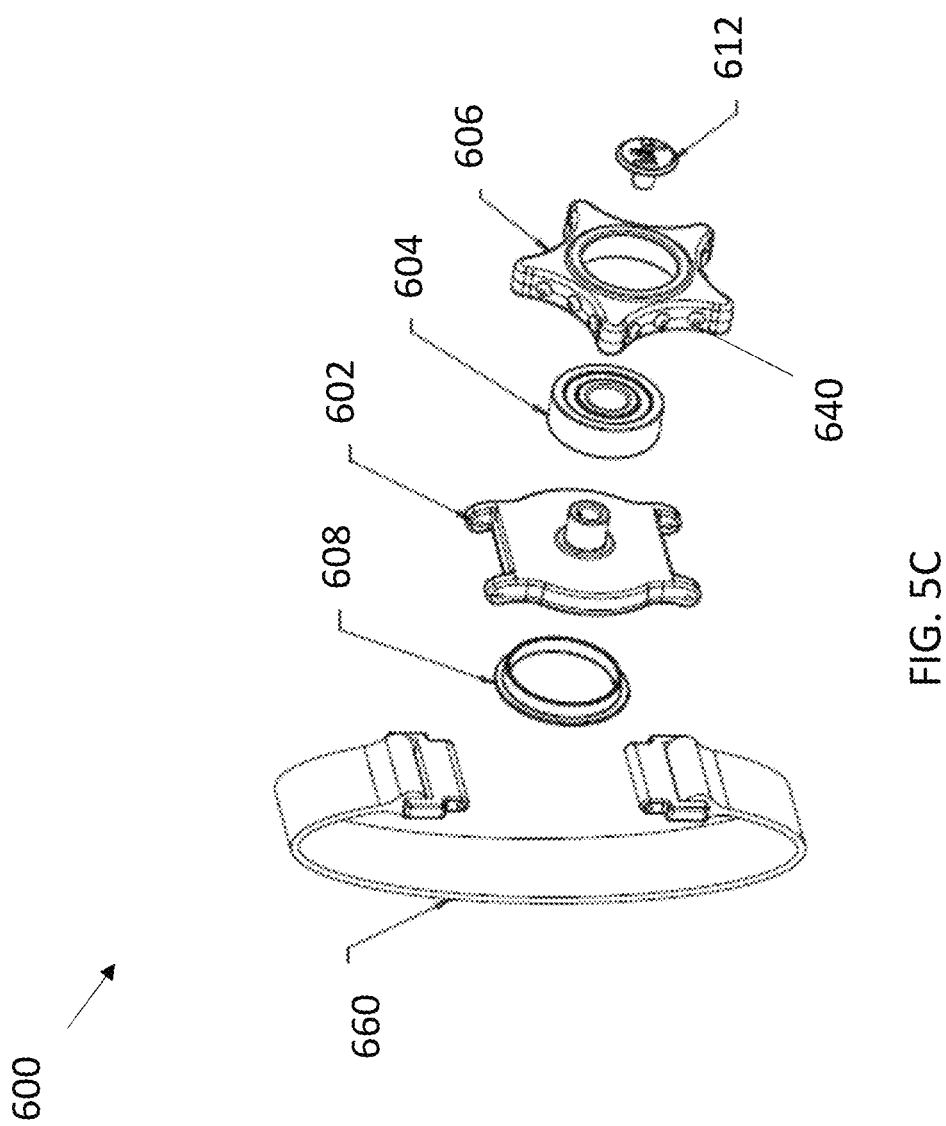
FIG. 5C shows an exploded view of the wearable device of FIG. 5A.
Figure 6A:
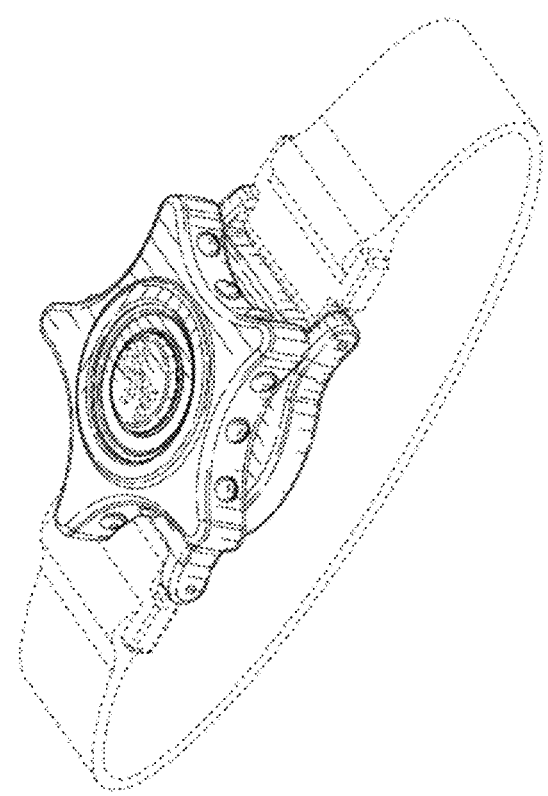
FIGS. 6A-6G show the ornamental design for a wearable fidget spinner, similar to FIGS. 5A-5C, as shown and described.
Figure 6C:
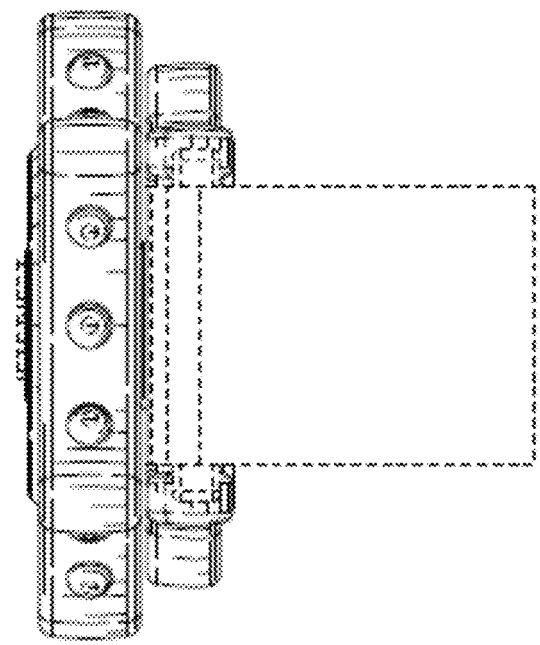
Figure 6B:
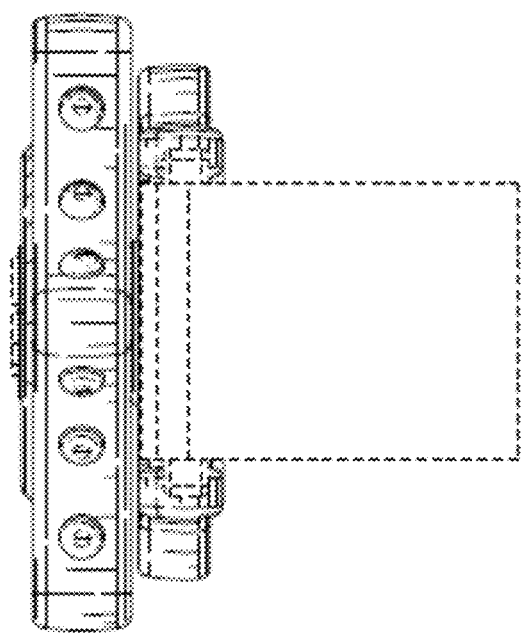
Figure 6D:
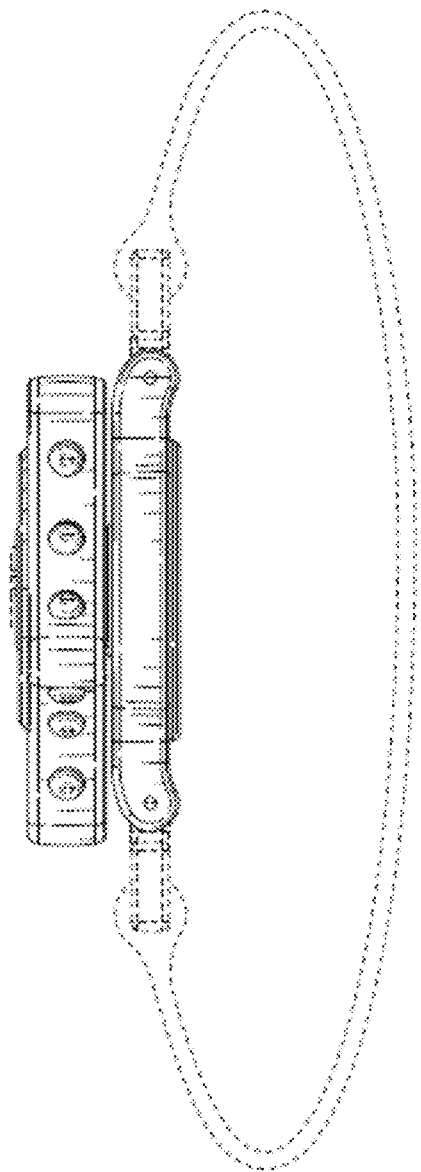
Figure 6E:
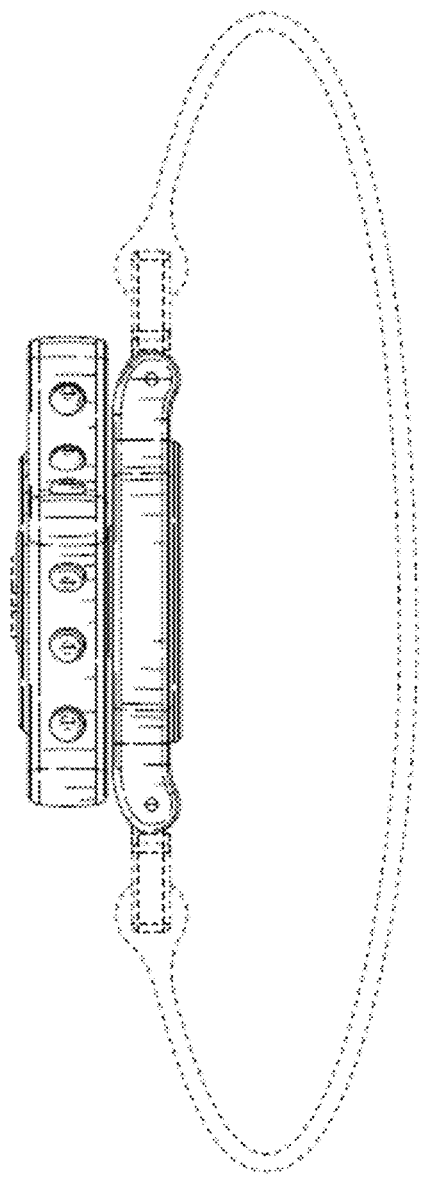
Figure 6F:
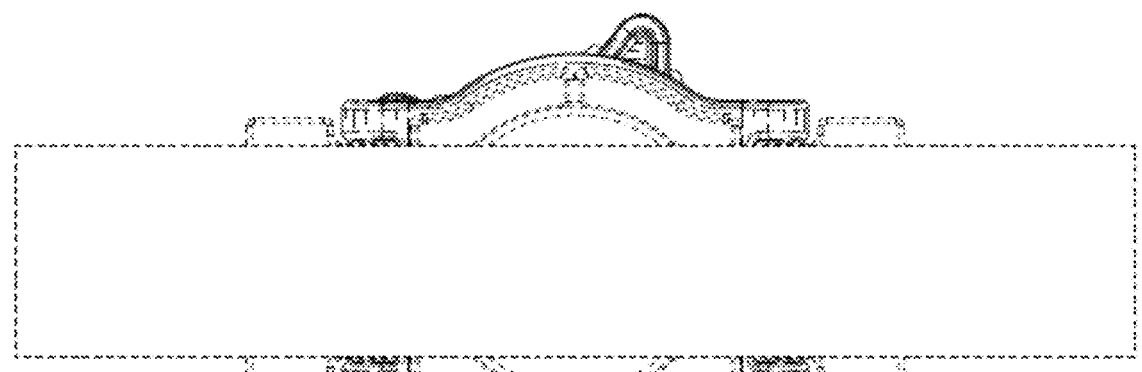
Figure 6G:
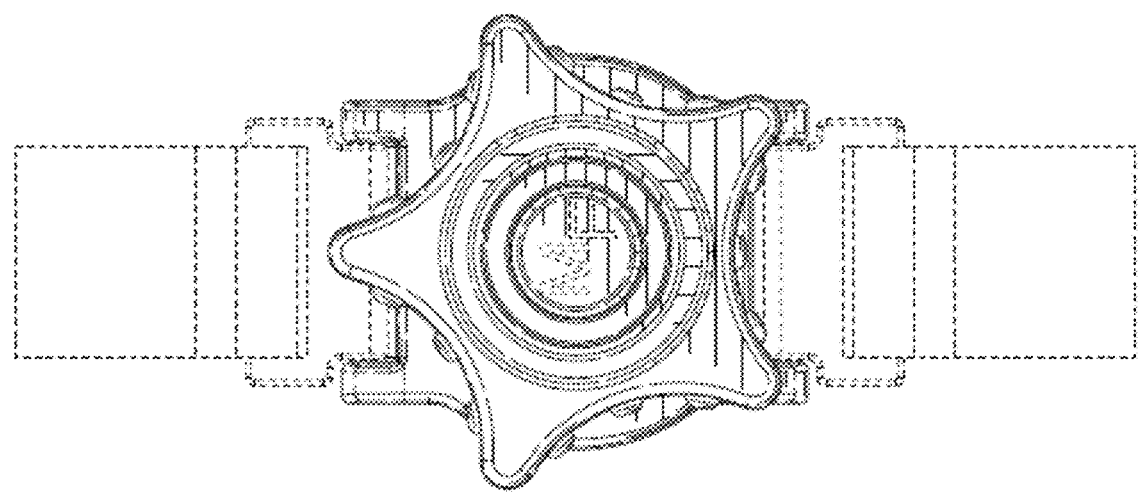
Figure 8B:
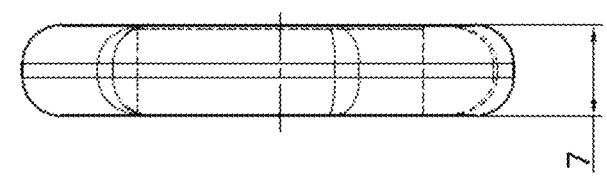
FIGS. 8A-8B show exemplary dimensions for a flower-shaped spinner.
Figure 8A:
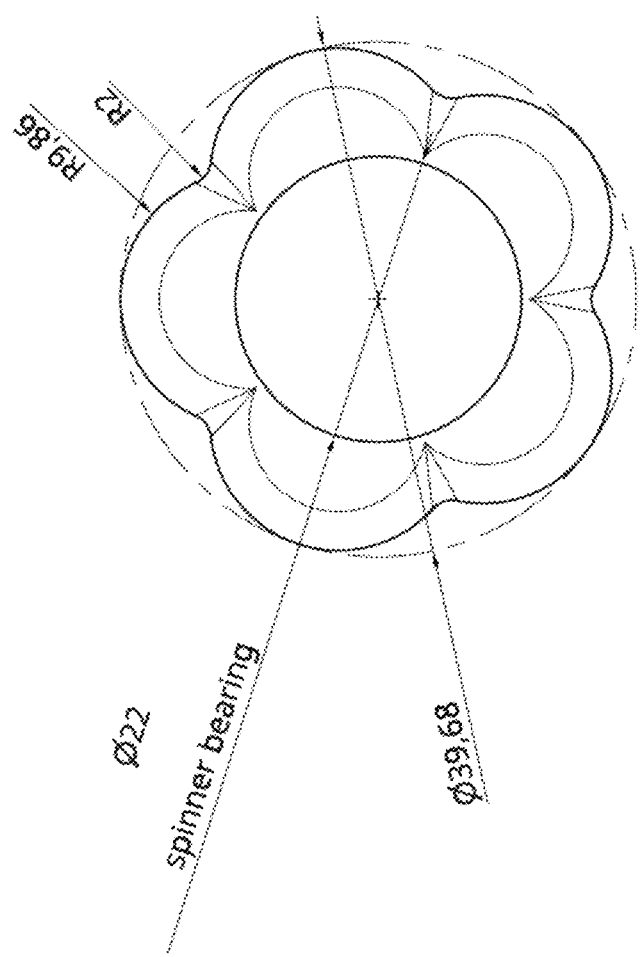
Figure 10C:
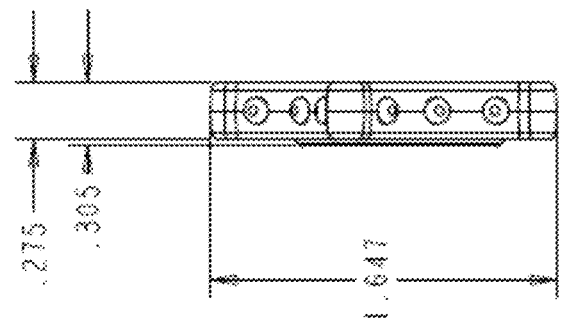
FIGS. 10A-10D show exemplary dimensions for another star-shaped spinner.
Figure 10B:
Figure 10D:
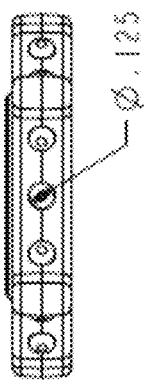
Figure 10A:
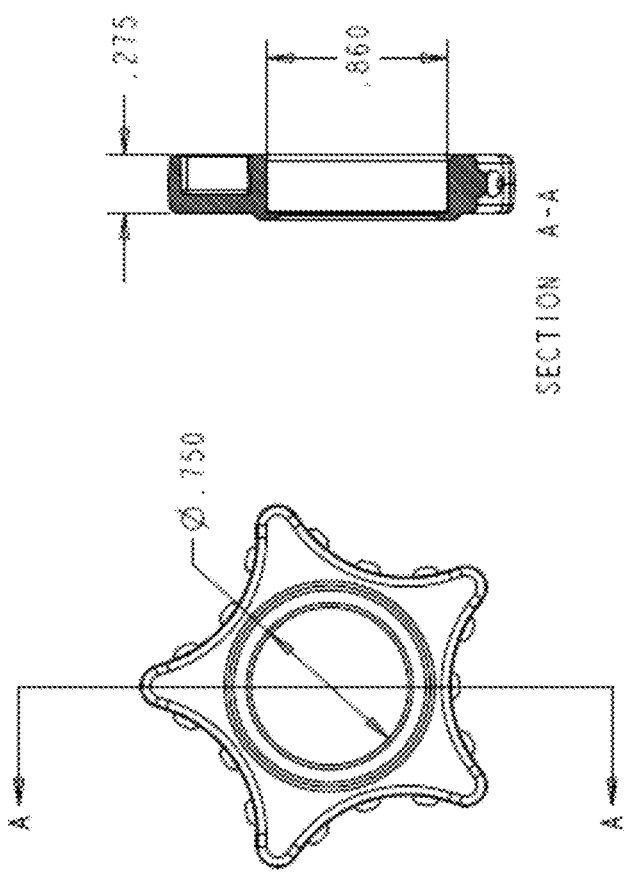
Figure 12C:
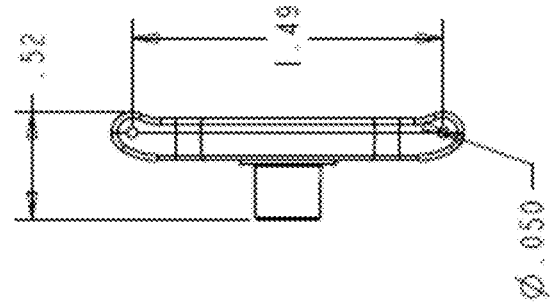
FIGS. 12A-12F show exemplary dimensions for various features of an exemplary base.
Figure 12B:
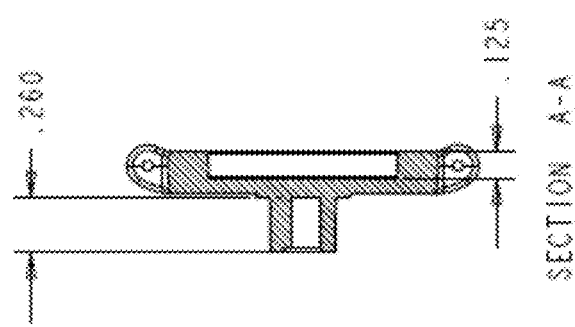
Figure 12A:
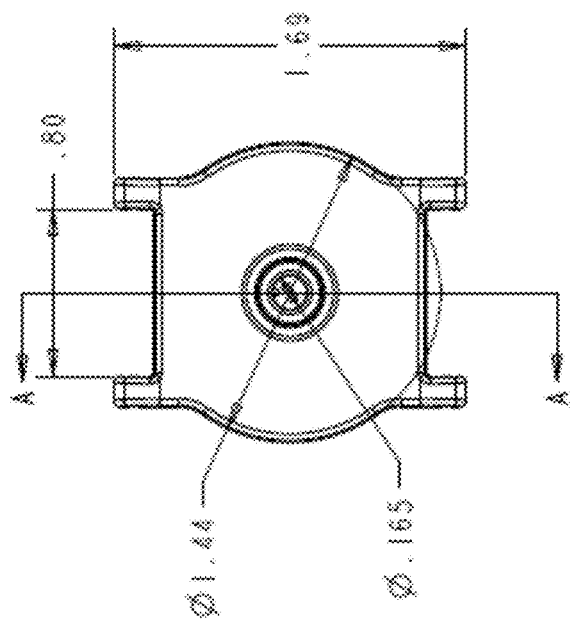
Figure 12F:
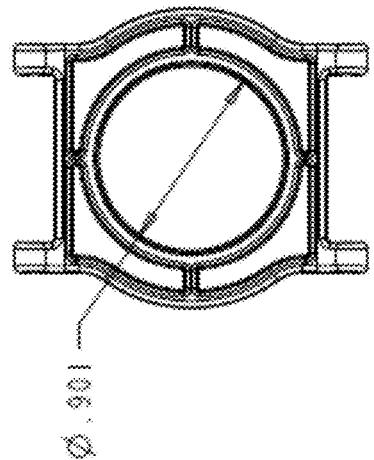
Figure 12E:
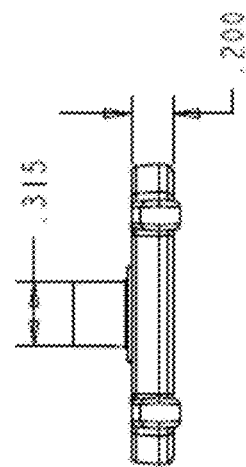
Figure 12D:
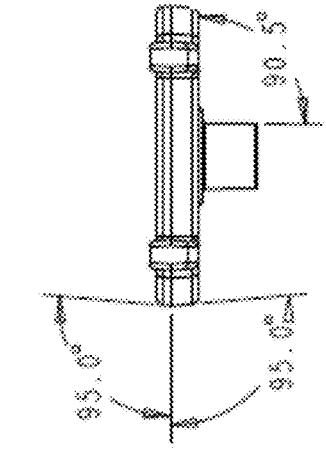

FIGS. 5A-5C (and 6A-6G) show another exemplary device 600 that is similar to device 400. Device 600 includes a spinner 606, a cap 612, a base 602, a rotating mechanism 604, a standoff 608, and a band 660. The spinner 606 is configured as a five-pointed star with tactile bumps 640 along the peripheral edges thereof. The band 660 can be, for example, a 20 mm woven nylon band with a Velcro closure. Similar to other embodiments, the rotating mechanism 604 can be a ball bearing, such as a 22 mm ball bearing. The rotating mechanism 604 can be coupled with, and configured to rotate about, a post 668 of the base 602.

FIGS. 7A-12F show exemplary dimensions (in inches unless otherwise indicated) of different embodiments. For example, FIGS. 7A-7B show exemplary dimensions of a triangular-shaped spinner, such as the spinner presented in FIGS. 3A-3D. FIG. 8A-8B show exemplary dimensions of a flower-shaped spinner, such as the spinner presented in FIGS. 1A-1E. FIG. 9A-9B show exemplary dimensions of a star-shaped spinner, such as the spinner presented in FIGS. 2A-2D. FIG. 10A-10D show exemplary dimensions of another star-shaped spinner, such as the spinner presented in FIGS. 5A-5C. FIG. 11A-C shows exemplary dimensions for various features of an exemplary base. FIGS. 12A-12F shows exemplary dimensions for various features of another exemplary base. The dimensions indicated in FIGS. 7A-12F are provided as examples only are not meant to limit the ranges of possible dimensions of a spinner and base.

It should be noted that the wearable devices described herein are not limited to those shown in FIGS. 1A-7G. For example, the devices need not attach to or include a wristband, but can instead or additionally include one or more attachment features for coupling with a chain, ring, belt, loop, pin and/or other wearable component. Further, the device can be configured to be worn on any part of the body (e.g., wrist, finger, neck, waist or hair) or clothing (e.g., shirt, pants, shoes or socks). Furthermore, the spinner shapes are not limited to those shown in FIGS. 1A-7G. For example, the spinner may have a circular, oval, polygonal (e.g., square, rectangle, hexagonal, octagonal, etc.), irregular (e.g., amoeba) peripheral shapes. The spinner may have sharp (e.g., uncurved) edges and/or rough surfaces.

The different shapes and/or features of the spinners described herein can advantageously provide unique tactile stimulations and different types of tactile exploration.

In some cases, the device (e.g., any devices shown in FIGS. 1A-7G) can provide visual stimulation. For instance, the shape and color(s) of the spinner may be visually appealing. In some cases, the spinning motion of the spinner can provide a strobe-like effect that some people may find helpful for managing stress. For example, various features (e.g., lobes 134, points 234, points 334 and/or bumps 340) can create a wagon-wheel effect when rotating, where these features can appear relatively motionless despite the continuous rotating motion of the spinner. In some instances, the various features e.g., lobes 134, points 234, points 334 and/or bumps 340) have colors that contrast their surroundings (e.g., remainder of the spinner) to accentuate the strobe-like effect.

In some embodiments, the wearable devices described herein can be used to treat, or complement treatment for, attention deficit hyperactivity disorder (ADHD), anxiety, depression, Specific Learning Disability (SLD), Alzheimer's, autism, akathisia, or other disorder. The user can wear the device and activate when necessary, such as via spinning, using tactile features, and/or obtaining visual stimulation.

When a feature or element herein is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wearable device, comprising:
   a band having a first end portion and a second end portion, the band configured to be placed around a user's wrist;
   a base having an upper surface with a first set of base attachment features and a second set of base attachment features, wherein the base is attached to the band by the first set of base attachment features, wherein the first set of attachment features is coupled to the first end portion and the second set of base attachment features is coupled to the second end portion, the upper surface comprising a post with a rotating mechanism adjacent to the upper surface, the rotating mechanism configured to rotate about the post, the base further comprising a first peripheral edge defining a base radius with respect to a center of the base; and
   a spinner coupled with the rotating mechanism and axially aligned with the base so as to rotate with respect to the center of the base, wherein the spinner includes a second peripheral edge that projects radially with respect to the first peripheral edge, wherein the second peripheral edge defines a spinner radius with respect to the center of the base, and wherein the spinner radius is about 5 percent to about 40 percent larger than the base radius.

2. The wearable device of claim 1, wherein the center of the base aligns with the axis of rotation of the rotating mechanism.

3. The wearable device of claim 1, wherein the base radius is measured laterally across the base.

4. The wearable device of claim 1, wherein the spinner comprises an outer surface with at least one tactile feature.

5. The wearable device of claim 4, wherein the at least one tactile feature includes a protrusion or a recess.

6. The wearable device of claim 4, wherein the at least one tactile feature is on the second peripheral edge.

7. The wearable device of claim 4, wherein the at least one tactile feature includes at least one recess along the second peripheral edge of the spinner, wherein a ratio of a depth of the at least one recess to a diameter of the spinner ranges from about 0.5 to about 1.

8. The wearable device of claim 4, wherein the at least one tactile feature includes at least one recess along the second peripheral edge of the spinner that defines a minimum diameter of the spinner and at least one protrusion along the second peripheral edge of the spinner that defines a maximum diameter of the spinner, wherein a ratio between the maximum diameter of the spinner to the minimum diameter of the spinner ranges from about 1.02 to about 1.06.

9. The wearable device of claim 4, wherein the at least one tactile feature is on a top surface of the spinner.

10. The wearable device of claim 1, wherein the spinner has a disc shape.

11. The wearable device of claim 1, wherein the second peripheral edge of the spinner forms a flower, a star or a triangle shape.

12. The wearable device of claim 1, wherein the rotating mechanism comprises a bearing assembly.

13. A method of treating a disorder using the wearable device of claim 1, the method comprising:
   applying the band of the wearable device to a wrist of a user;
   rotating the spinner about the base of the wearable device to provide a therapeutic effect; and rubbing or moving a tactile feature on the spinner to provide an additional therapeutic effect.

14. The method of claim 13, wherein the user suffers from attention deficit hyperactivity disorder (ADHD), anxiety, depression, specific learning disability (SLD), Alzheimer's, autism, or akathisia.

15. The method of claim 13, wherein the therapeutic effect is relief of stress, reducing excess energy, or reducing symptoms of the disorder.

16. The method of claim 13, wherein the tactile feature is a bump on a peripheral edge of the spinner.

17. A wearable device, comprising:
   a band having a first end portion and a second end portion, the band configured to be placed around a user's wrist;
   a base having an upper surface with a first set of base attachment features and a second set of base attachment features, wherein the first set of base attachment features is coupled to the band first end portion and the second set of base attachment features is coupled to the band second end portion, wherein a post is positioned on the upper surface of the base, the post comprising a rotating mechanism configured to rotate about the post, the base including a first peripheral edge defining a base radius with respect to a center of the base; and
   a spinner coupled with the rotating mechanism so as to rotate about the post on the upper surface of the base, wherein the spinner includes a second peripheral edge that projects radially with respect to the first peripheral edge, and further wherein the spinner includes at least one tactile sensory feature thereon.

18. The wearable device of claim 17, wherein the center of the base aligns with the axis of rotation of the rotating mechanism.

19. The wearable device of claim 17, wherein the spinner comprises an outer surface with the at least one tactile sensory feature.

20. The wearable device of claim 19, wherein the at least one tactile sensory feature includes a protrusion or a recess.

21. The wearable device of claim 19, wherein the at least one tactile sensory feature is on the second peripheral edge.

22. The wearable device of claim 19, wherein the at least one tactile sensory feature includes at least one recess along the second peripheral edge of the spinner, wherein a ratio of a depth of the at least one recess to a diameter of the spinner ranges from about 0.01 to about 0.03.

23. The wearable device of claim 17, wherein the at least one tactile sensory feature includes at least one recess along the second peripheral edge of the spinner that defines a minimum diameter of the spinner and at least one protrusion along the second peripheral edge of the spinner that defines a maximum diameter of the spinner, wherein a ratio between the maximum diameter to the minimum diameter ranges from about 1.02 to about 1.06.

24. The wearable device of claim 17, wherein the at least one tactile sensory feature is on a top surface of the spinner.

25. The wearable device of claim 17, wherein the spinner has a disc shape.

26. The wearable device of claim 17, wherein the rotating mechanism comprises a bearing assembly.

27. The wearable device of claim 17, wherein the second peripheral edge of the spinner forms a flower, a star or a triangle shape.

* * * * *